(12) United States Patent
Holsten et al.

(10) Patent No.: US 10,575,977 B2
(45) Date of Patent: Mar. 3, 2020

(54) GASTRIC TUBES AND METHODS OF USE

(71) Applicant: Covidien LP, Mansfield, MA (US)

(72) Inventors: Henry Holsten, Hamden, CT (US); Thomas Wenchell, Durham, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/166,995

(22) Filed: Oct. 22, 2018

(65) Prior Publication Data

US 2019/0053929 A1 Feb. 21, 2019

Related U.S. Application Data

(63) Continuation of application No. 15/496,193, filed on Apr. 25, 2017, now Pat. No. 10,111,772, which is a
(Continued)

(51) Int. Cl.
*A61F 5/00* (2006.01)
*A61B 1/06* (2006.01)
(Continued)

(52) U.S. Cl.
CPC .............. *A61F 5/0089* (2013.01); *A61B 1/06* (2013.01); *A61B 17/0218* (2013.01); *A61B 17/30* (2013.01); *A61F 5/0076* (2013.01); *A61F 5/0083* (2013.01); *A61B 2017/00566* (2013.01); *A61B 2017/00818* (2013.01);
(Continued)

(58) Field of Classification Search
CPC .................. A61B 17/0218; A61B 1/06; A61B 2017/00818; A61F 5/0076; A61F 5/0083; A61F 5/0089
See application file for complete search history.

(56) References Cited

U.S. PATENT DOCUMENTS

| | | | |
|---|---|---|---|
| 4,328,805 A | 5/1982 | Akopov et al. | |
| 4,403,604 A | 9/1983 | Wilkinson et al. | |

(Continued)

FOREIGN PATENT DOCUMENTS

| | | |
|---|---|---|
| CN | 201365906 Y | 12/2009 |
| CN | 102626536 A | 8/2012 |

(Continued)

OTHER PUBLICATIONS

Co-Pending U.S. Appl. No. 14/276,303; Rokde el al., Covidien LP, Claim set added on Mar. 3, 2016.
(Continued)

*Primary Examiner* — Christine H Matthews
(74) *Attorney, Agent, or Firm* — Carter, DeLuca & Farrell, LLP

(57) ABSTRACT

A gastric tube for use in a bariatric surgical procedure includes an elongate tube and a movable component supported on an outer surface of the elongate tube. The elongate tube has a non-circular cross section along at least a portion of a length of the elongate tube. The movable component is movable between an unexpanded configuration and an expanded configuration. In the unexpanded configuration, the movable component is disposed in abutting engagement with the outer surface of the elongate tube. In the expanded configuration, the movable component bows outwardly from the outer surface of the elongate tube.

18 Claims, 5 Drawing Sheets

Related U.S. Application Data continuation of application No. 14/334,730, filed on Jul. 18, 2014, now Pat. No. 9,629,741.

(51) Int. Cl.
*A61B 17/02* (2006.01)
*A61B 17/30* (2006.01)
*A61B 17/00* (2006.01)

(52) U.S. Cl.
CPC ... *A61B 2017/306* (2013.01); *A61B 2217/005* (2013.01); *A61B 2217/007* (2013.01)

(56) References Cited

U.S. PATENT DOCUMENTS

| | | |
|---|---|---|
| 4,733,669 A | 3/1988 | Segal |
| 5,179,938 A | 1/1993 | Lonky |
| 5,246,456 A | 9/1993 | Wilkinson |
| 5,297,536 A | 3/1994 | Wilk |
| 5,382,231 A | 1/1995 | Shlain |
| 5,401,241 A | 3/1995 | Delany |
| 5,458,131 A | 10/1995 | Wilk |
| 5,465,709 A | 11/1995 | Dickie et al. |
| 5,718,666 A | 2/1998 | Alarcon |
| 7,153,131 B2 | 12/2006 | Crohn |
| 8,092,378 B2 | 1/2012 | Roth et al. |
| 8,147,502 B2 | 4/2012 | Albrecht et al. |
| 8,192,448 B2 | 6/2012 | Bessler et al. |
| 8,454,503 B2 | 6/2013 | Roth et al. |
| 8,663,149 B2 | 3/2014 | Gagner et al. |
| 9,629,741 B2 | 4/2017 | Holsten et al. |
| 10,111,772 B2 | 10/2018 | Holsten et al. |
| 2002/0091395 A1 | 7/2002 | Gabbay |
| 2002/0183768 A1 | 12/2002 | Deem et al. |
| 2004/0006351 A1 | 1/2004 | Gannoe et al. |
| 2004/0092974 A1 | 5/2004 | Gannoe et al. |
| 2005/0119674 A1 | 6/2005 | Gingras |
| 2005/0203489 A1 | 9/2005 | Saadat et al. |
| 2005/0251158 A1 | 11/2005 | Saadat et al. |
| 2006/0106288 A1 | 5/2006 | Roth et al. |
| 2006/0200004 A1 | 9/2006 | Wilk |
| 2006/0241344 A1 | 10/2006 | Wilk |
| 2006/0241570 A1 | 10/2006 | Wilk |
| 2006/0258902 A1 | 11/2006 | Spivey et al. |
| 2007/0032702 A1 | 2/2007 | Ortiz |
| 2009/0276055 A1 | 11/2009 | Harris et al. |
| 2010/0179417 A1 | 7/2010 | Russo |
| 2011/0178454 A1 | 7/2011 | Gagner et al. |
| 2011/0288576 A1 | 11/2011 | Hoffman |
| 2012/0165608 A1 | 6/2012 | Banik et al. |
| 2012/0184981 A1 | 7/2012 | Pecor et al. |
| 2012/0232339 A1* | 9/2012 | Csiky .................. A61B 34/30 600/104 |
| 2012/0239061 A1 | 9/2012 | Mathur |
| 2013/0165774 A1 | 6/2013 | Nocca |
| 2014/0018722 A1 | 1/2014 | Scott et al. |
| 2014/0114121 A1 | 4/2014 | Trivedi |

FOREIGN PATENT DOCUMENTS

| | | |
|---|---|---|
| EP | 2246013 A1 | 11/2010 |
| EP | 2407200 A1 | 1/2012 |
| ES | 2326937 A1 | 10/2009 |
| JP | 3178309 U | 9/2012 |
| WO | 02096327 A2 | 12/2002 |
| WO | 03075979 A2 | 9/2003 |
| WO | 2009097585 A1 | 8/2009 |
| WO | 2012138737 A1 | 10/2012 |
| WO | 2013123235 A1 | 8/2013 |
| WO | 2014062881 A1 | 4/2014 |

OTHER PUBLICATIONS

Extended European Search Report dated Sep. 17, 2015, corresponding to European Patent Application 15167339.9; 10 pages.

Extended European Search Report dated Oct. 1, 2015, corresponding to European Application No. 15167342.3; 7 pages.

European Search Report dated Dec. 2, 2015, corresponding to European Application No. 151772332; 7 pages.

Dietel et al., "Endoscopy of Vertical Banded Gastroplasty," The American Surgeon, May 1989, vol. 55; pp. 287-890.

Dietel et al., "Vertical Banded Gastroplasty: Results in 233 Patients," The Canadian Journal of Surgery, Sep. 1986, vol. 29, No. 5; pp. 322-324.

Mason et al., "Vertical Gastroplasty: Evolution of Vertical Banded Gastroplasty,"World Journal of Surgery, Sep. 1998, vol. 22, No. 9; pp. 919-924.

European Search Report, dated Mar. 19, 2015, corresponding to European Application No. 14192226.0; 7 pages.

European Search Report, dated Mar. 24, 2015, corresponding to European Application No. 14192416.7; 7 pages.

International Search Report and Written Opinion of hte International Searching Authoirity, dated Jul. 12, 2016, corresponding to International ApplicationNo. PCT/US2016/028046; 12 total pages.

European Communication dated Mar. 24, 2017, corresponding to European Application No. 15177233.2; 4 pages.

\* cited by examiner

GASTRIC TUBES AND METHODS OF USE

CROSS-REFERENCE TO RELATED APPLICATION(S)

This application is a continuation application of U.S. patent application Ser. No. 15/496,193, filed on Apr. 25, 2017, which is a continuation application of U.S. patent application Ser. No. 14/334,730, filed on Jul. 18, 2014, now U.S. Pat. No. 9,629,741, the entire contents of each of which being incorporated by reference herein.

TECHNICAL FIELD

The present disclosure generally relates to surgical instruments, and more particularly, to gastric tubes used in bariatric procedures.

BACKGROUND

Obesity is reaching epidemic proportions in many regions of the world, particularly in the United States. In order to treat obesity, various bariatric procedures have been developed including, for example, gastric bypass, adjustable gastric banding, and sleeve gastrectomy. The goal in each of these procedures is to reduce the stomach capacity to restrict the amount of food that the patient can eat. The reduced stomach capacity, in turn, results in a feeling of fullness for the patient after ingesting a relatively smaller amount of food. Thus, the patient can achieve significant weight loss.

Sleeve gastrectomy involves transecting a stomach, e.g., using a stapling device or other suitable device, to reduce a stomach volume. Sleeve gastrectomy procedures are often aided by the use of a gastric tube, which serves as a guide or template for transecting the stomach to the appropriate configuration while inhibiting inadvertent transection of stomach or esophageal tissue. Once the stomach has been appropriately transected, the gastric tube is removed and a leak test is performed to determine whether there are any areas of extravasation.

In use, the gastric tube may be advanced into a patient's body through an oral cavity and down through the esophagus into the stomach to provide delineation of the antrum of the stomach, irrigation/suction of fluids, and/or a sizing of a gastric pouch. While being advanced, due at least in part to the circuitous nature of this track, a clinician may need to reposition the gastric tube in various orientations until the gastric tube is properly aligned or bypasses any obstruction(s).

Accordingly, increasing visibility and maneuverability of the gastric tube within a patient's body could aid in navigating the gastric tube to its selected final position within the patient's body, maintaining the gastric tube in its selected final position, and/or reduce the time to perform a desired procedure.

SUMMARY

According to one aspect of the present disclosure, a gastric tube for use in a bariatric surgical procedure is provided. The gastric tube includes an elongate tube and a movable component. The elongate tube has a non-circular cross section along at least a portion of its length. The elongate tube includes an outer surface, a proximal end portion, a distal end portion, and a lumen defined along the length of the elongate tube. The proximal end portion defines an opening therein configured to be coupled with a vacuum source. The distal end portion has a blunt tip. The lumen is in communication with the opening of the proximal end portion. The movable component is supported on the outer surface and is movable between an unexpanded configuration in which the movable component is disposed in abutting engagement with the outer surface and an expanded configuration in which the movable component bows outwardly from the outer surface of the elongate tube.

In embodiments, the non-circular cross section may be a U-shaped configuration or a V-shaped configuration.

In embodiments, the outer surface may define a groove therein extending along at least a portion of the length of the elongate tube. The proximal portion of the movable component may be slidably disposed within the groove. The movable component may have a distal end that is fixedly coupled to the distal end portion of the elongate tube. The movable component may be a sail member. The sail member may have a plurality of lights disposed thereon. An entirety of the sail member may be disposed within the groove when the sail member is in the unexpanded configuration.

In embodiments, the outer surface may have an arcuate portion extending along the length of the elongate tube and a planar portion extending along the length of the elongate tube. The groove may be defined in the planar portion. The movable component may include a proximal portion. The groove may be configured to retain the proximal portion of the movable component therein.

In embodiments, the blunt tip may define an opening formed therein configured and dimensioned for at least one of aspiration or irrigation.

In another aspect of the present disclosure, a method of performing bariatric surgery is provided. The method includes providing a gastric tube and inserting the gastric tube into an oral cavity of a patient. The gastric tube is guided along an enteral pathway and repositioned based on an observed position of an outer surface to a selected position within a stomach of the patient. A movable component of the gastric tube is moved from an unexpanded configuration to an expanded configuration in which the movable component bows outwardly from the outer surface of the elongate tube into engagement with a portion of the stomach. A portion of the stomach is then transected.

In embodiments, guiding the gastric tube along the enteral pathway may include advancing the gastric tube from an oral cavity through an esophagus into an antrum of the stomach.

In embodiments, moving the movable component may include sliding the movable component distally relative to the elongate tube and through a groove defined in the outer surface.

In embodiments, the method may further include adjusting a configuration of the sail member in response to an observed configuration of the sail member.

Other aspects, features, and advantages of the present disclosure will be apparent from the description, the drawings, and the claims.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

As used herein, the term "clinician" refers to a doctor, nurse, or other care provider and may include support personnel. The terms "proximal" or "trailing" each refer to the portion of a structure closer to a clinician, and the terms "distal" or "leading" each refer to a portion of a structure farther from the clinician.

Figure 1:
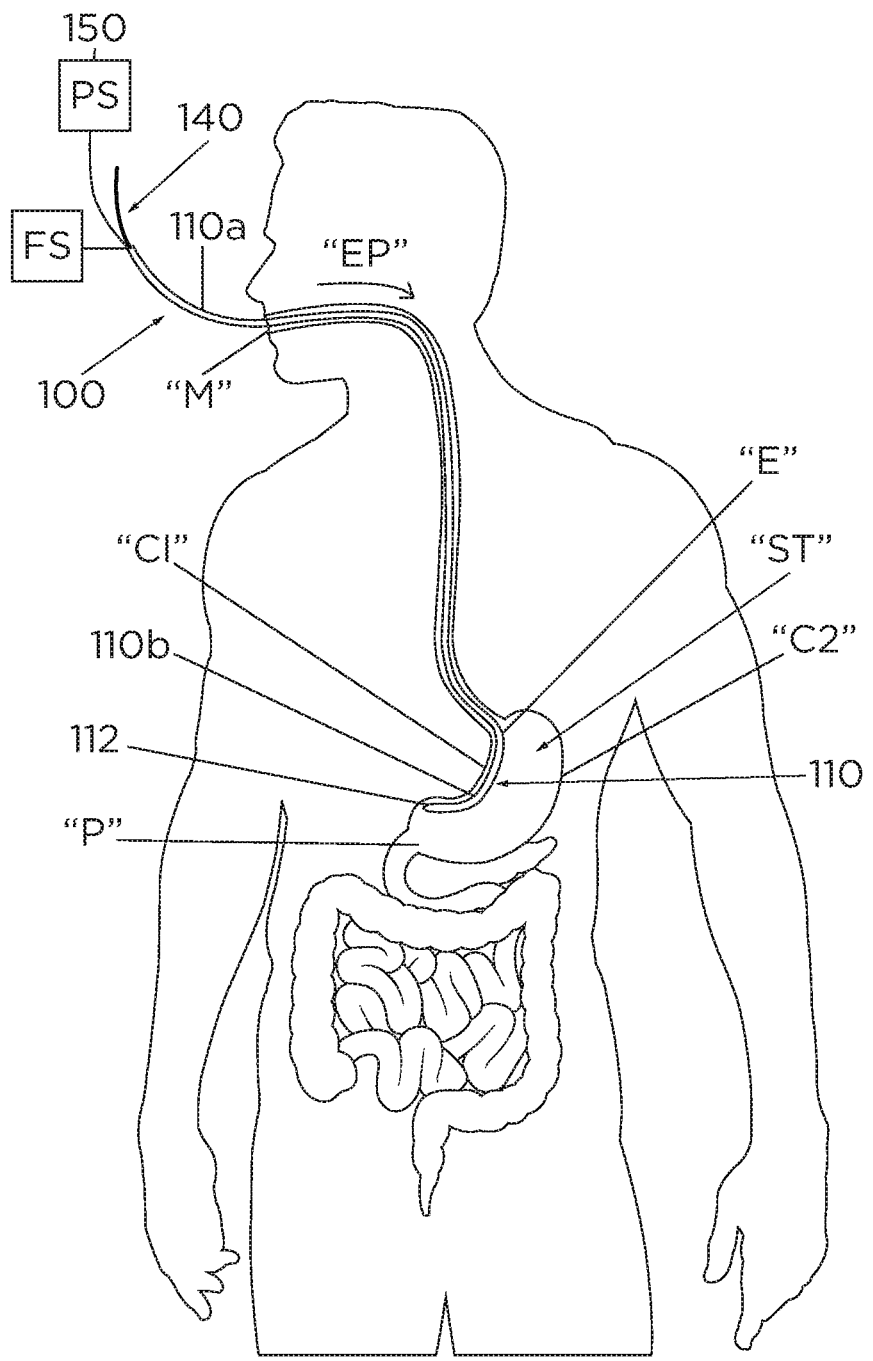
FIG. 1 is a side view of an illustrative embodiment of a gastric tube being navigated through an enteral pathway of a patient into a stomach of a patient in accordance with the principles of the present disclosure.

Referring now to FIG. 1, a gastric tube 100 includes a non-circular elongate tube 110, a movable component, such as, for example, a sail member 140 supported on the elongate tube 110, and a power source 150 coupled to a plurality of light sources 148 (FIG. 2) associated with sail member 140.

In use, as described in further detail below with reference to FIG. 1, gastric tube 100 is inserted into an oral cavity (e.g., a mouth "M") of a patient and is advanced distally (i.e., caudally) along an enteral pathway "EP" that includes a track that extends between oral cavity "M" and a stomach "ST" of the patient. The light sources 148 (FIG. 2) illuminate sail member 140 so as to aid a clinician in guiding the gastric tube 100 along the enteral pathway "EP." The non-circular configuration of elongate tube 110 inhibits elongate tube 110 from unwanted rotation when being guided along enteral pathway "EP" and provides a visual reference to the clinician as gastric tube 100 is navigated along enteral pathway "EP." When positioned in the stomach "ST" of the patient (e.g., the antrum or lower part of the stomach), sail member 140 can be expanded or bowed outwardly into abutment with the stomach "ST" and, in turn, pressingly engage elongate tube 110 with an opposite side of stomach "ST" and aid the clinician in performing a bariatric surgical procedure such as a sleeve gastrectomy.

Figure 2:
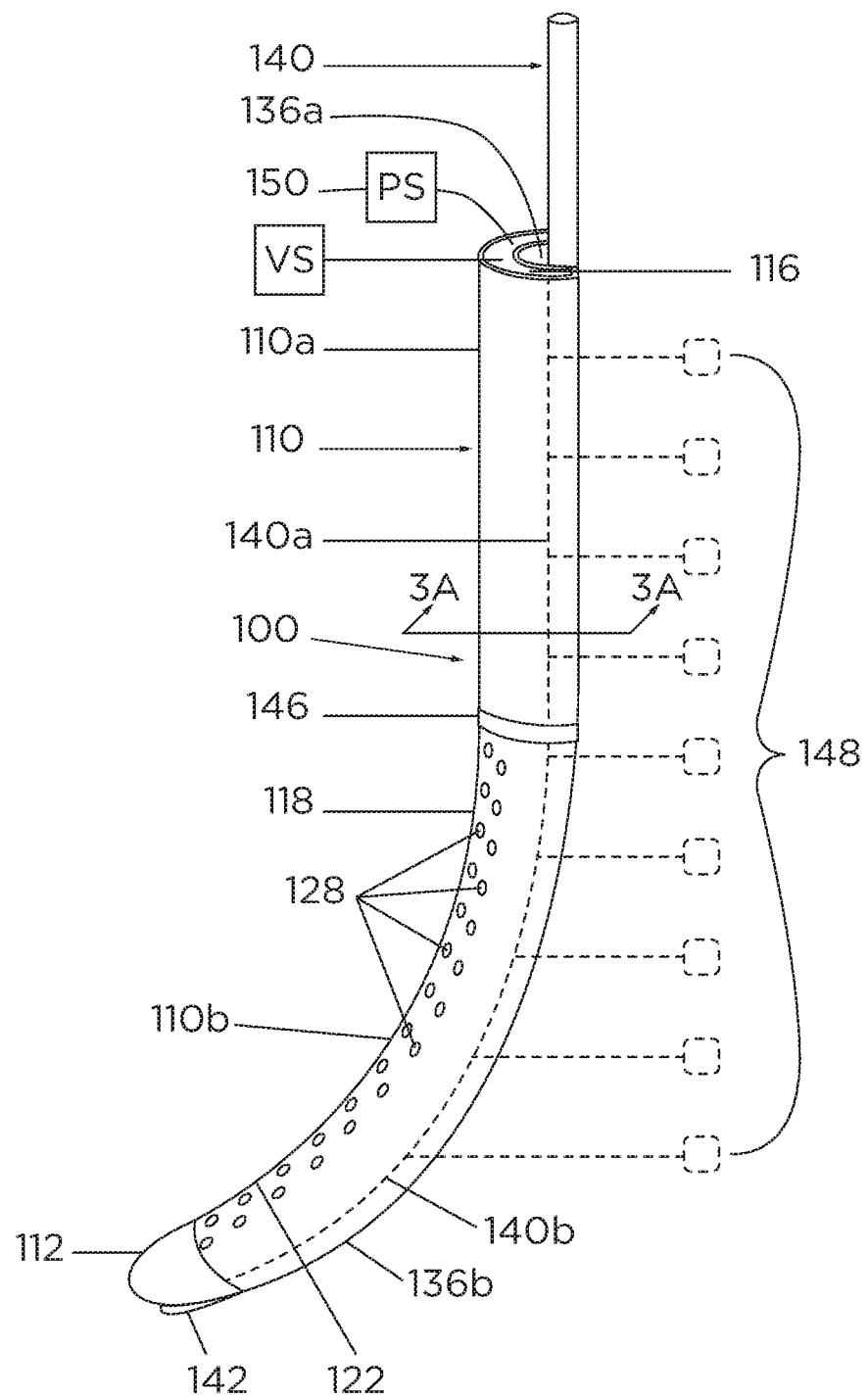
FIG. 2 is a perspective view of the gastric tube of FIG. 1 and a movable component thereof disposed in an unexpanded position.
Figure 3A:
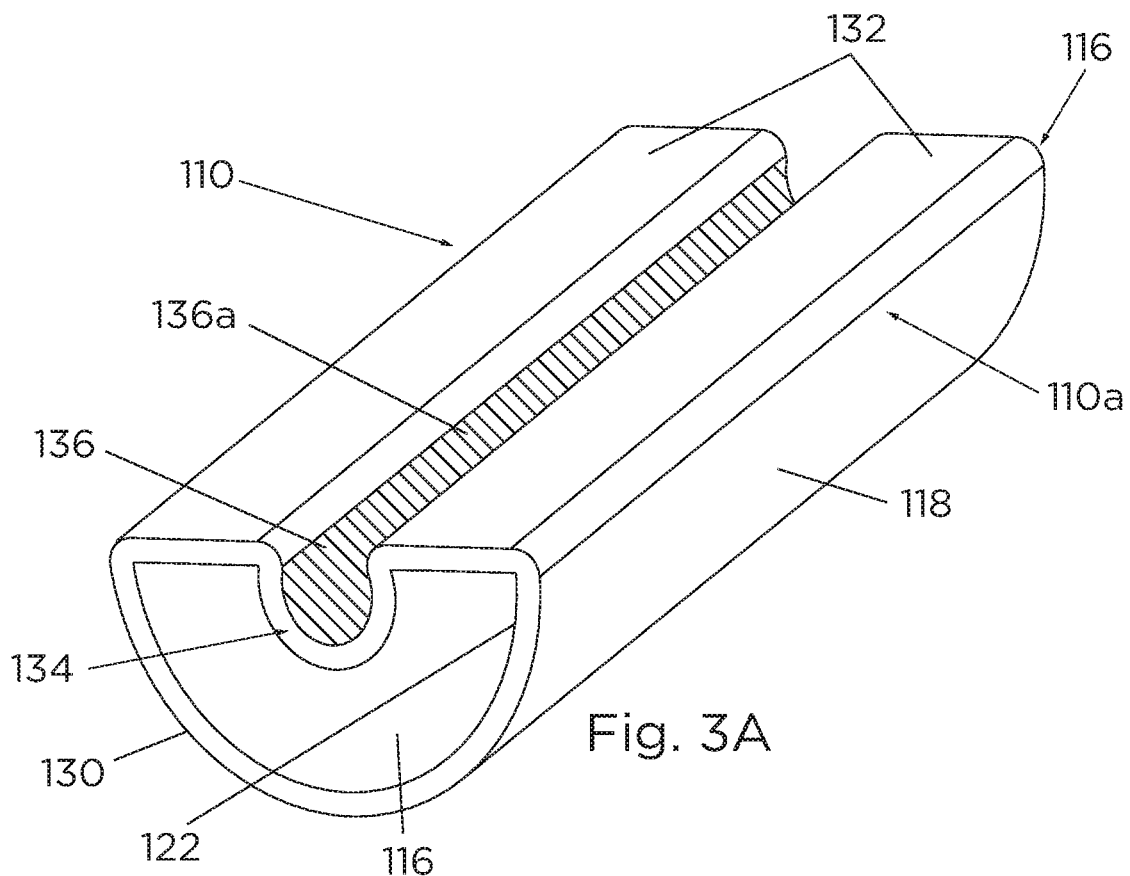
FIG. 3A is an enlarged, perspective view of a cross-section, taken along line 3A-3A of FIG. 2, of an elongate tube of the gastric tube of FIG. 2.

With reference to FIGS. 1 and 3A, elongate tube 110 can be formed of any material with sufficient flexibility to enable elongate tube 110 to maneuver along the patient's track or enteral pathway "EP" between the oral cavity "M" and the stomach "ST." Elongate tube 110 includes a trailing end portion or proximal end portion 110a and a leading end portion or distal end portion 110b. Elongate tube 110 extends between the proximal and distal end portions 110a, 110b. It is contemplated that elongate tube 110 can be curved along its length, linear, or any shape suitable for a particular bariatric surgical procedure. Elongate tube 110 defines a lumen 116 extending along and through the length of elongate tube 110. Elongate tube 110 further includes a plurality of openings or apertures 128 (FIGS. 2 and 4) extending between an outer surface 118 and an inner surface 122 of elongate tube 110. Apertures 128 provide for fluid communication between lumen 116 and an environment exterior to elongate tube 110. When suction is applied to elongate tube 110, elongate tube 110 can adhere to tissue, such as, for example, stomach tissue, due to the plurality of openings 128 directing suction towards stomach tissue. Suction is applied through lumen 116 and apertures 128

Proximal end portion 110a of elongate tube 110 has an opening 116 configured for connection with a vacuum source "VS" (FIG. 2) and/or a fluid source "FS" (FIG. 1). Distal end portion 110b includes a distal tip 112. Distal tip 112 has a blunt, arcuate outer surface such that advancement of elongate tube 110 through internal body cavities of a patient allows the elongate tube 110 to follow the track of the body cavities while inhibiting penetration by the distal tip 112 (i.e., distal tip 112 is configured for atraumatic insertion). In some embodiments, distal tip 112 can be variously configured, such as, for example, oval, oblong, tapered, uniform, non-uniform, smooth, polished, and/or rounded.

Figure 3B:
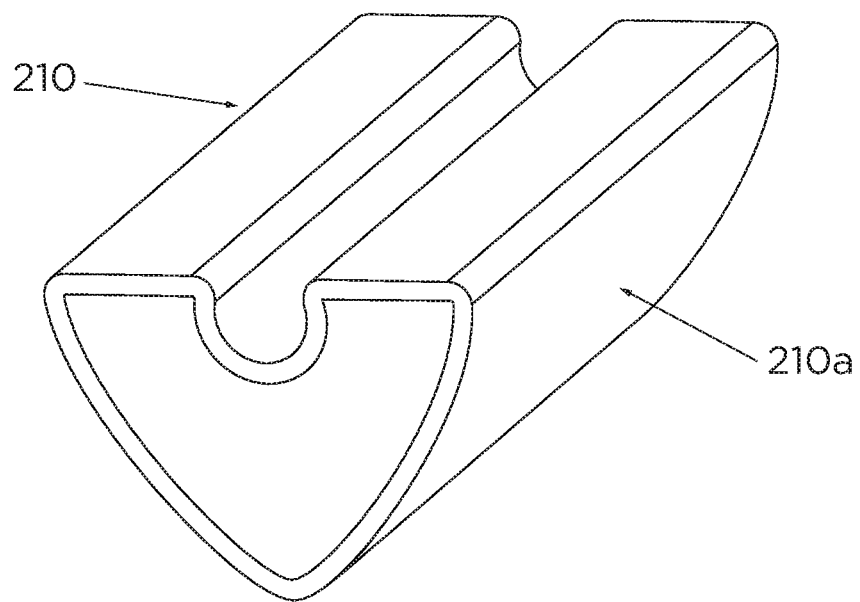
FIG. 3B is an enlarged, perspective view of another embodiment of the portion of the elongate tube shown in FIG. 3A.

With reference to FIGS. 3A and 3B, elongate tube 110 has a non-circular cross-section configuration along at least a portion of its length. In one embodiment, as shown in FIG. 3A, elongate tube 110 has a U-shaped cross-sectional configuration. In another embodiment, as shown in FIG. 3B, an elongate tube 210, similar to elongate tube 110 has proximal portion 210a having a V-shaped cross-sectional configuration. In some embodiments, elongate tube 110 has various non-circular cross-sectional configurations, such as, for example, rectangular, square, star-shaped, kidney-bean shaped, polygonal, uniform, non-uniform, or the like.

With reference to FIG. 3A, outer surface 118 of elongate tube 110 has a convex or arcuate portion 130 extending longitudinally along elongate tube 110 and a substantially planar portion 132 extending longitudinally along elongate tube 110. Outer surface 118 further includes a concave depression 134 formed in planar portion 132. Depression 134 extends longitudinally along a central location of planar portion 132 such that planar portion 132 is divided into two planar segments separated by depression 134.

Depression 134 defines a groove 136 defined in outer surface 118 and configured for slidable receipt of sail member 140. Groove 136 houses sail member 140 to decrease an overall diameter of gastric tube 100 and to provide a track along which sail member 140 can traverse during actuation of sail member 140, as described in greater detail below. In embodiments, groove 136 may extend longitudinally along proximal end portion 110a of elongate tube 110 only or proximal end portion 110a and distal end portion 110b of elongate tube 110. Sail member 140 resides in groove 136 such that sail 140 is flush with planar portion 132. In embodiments, sail member 140 may be below planar portion 132 or above planar portion 132.

Groove 136 has a proximal portion 136a defined in proximal end portion 110a of elongate tube 110 and a distal portion 136b (FIGS. 2 and 4) defined in distal end portion 110b of elongate tube 110. Proximal portion 136a of groove 136 is omega-shaped such that proximal portion 136a of groove 136 is configured to retain a proximal portion 140a of sail member 140 therein. Distal portion 136b of groove 136 has a continuously concave configuration such that distal portion 136b of groove 136 is configured to permit a distal portion 140b of sail member 140 to move out of groove 136 without obstruction. In embodiments, groove 136 may be variously configured, such as, for example, arcuate, square, triangular, U-shaped, V-shaped, polygonal, or the like.

Figure 4:
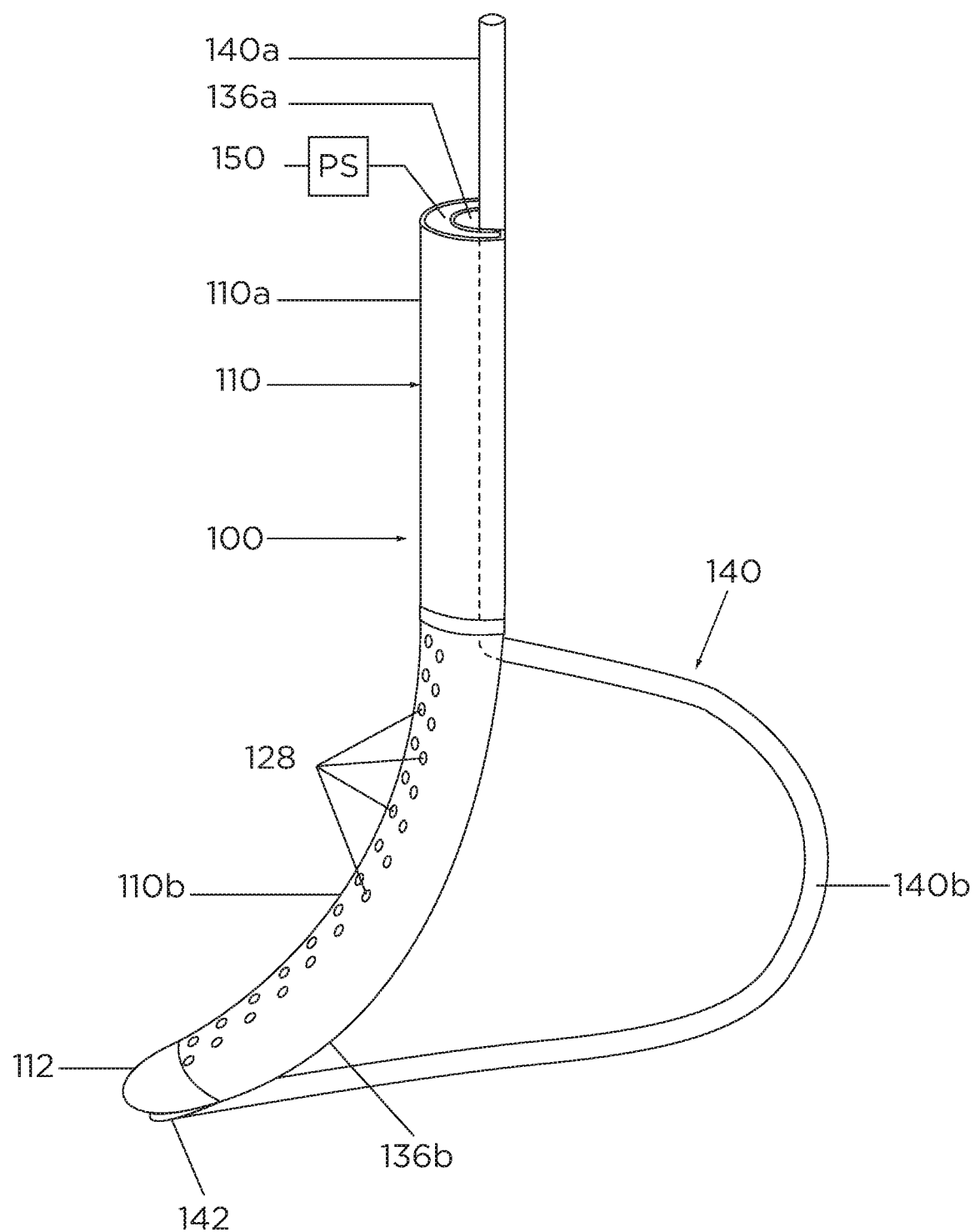
FIG. 4 is perspective view of the gastric tube of FIG. 2 with the movable component disposed in an expanded position.

With reference to FIGS. 2 and 4, sail member 140 is formed from a semi-rigid, resiliently flexible material, e.g., a suitable elastomer, and may be in the form of a rod. Sail member 140 defines a length greater than the length of elongate tube 110 such that sail member 140 can be accessed outside the patient and/or remotely of the surgical site. Sail member 140 is supported on elongated tube 110. In particular, sail member 140 is slidingly received within groove 136 of elongate tube 110. In embodiments, sail member 140 may be attached to elongate tube 110 via various fastening engagements, such as, for example, adhesively attached, welded, or integrally formed with elongate tube 110. As mentioned above, sail member 140 includes a proximal portion 140a and a distal portion 140b. Proximal portion 140a of sail member 140 is slidingly captured within proximal portion 136a of groove 136. Distal portion 140b of sail member 140 is releasably disposed within distal portion 136b of groove 136. Distal portion 140b of sail member 140 has a distal end 142 that is integrally, i.e., monolithically, formed with or otherwise fixedly coupled to distal tip 112 of elongate tube 110 such that distal movement of sail member 140 causes distal portion 140b of sail member 140 to expand or bow outwardly relative to elongate tube 110, as described in greater detail below. A coupling 146, e.g., a ring, sleeve, hook, latch, etc., may be affixed to elongate tube 110 and surround an intermediate portion of sail member 140 to facilitate the coupling of sail member 140 to elongate tube 110.

Sail member 140 is slidable through proximal portion 136a of groove 136 and coupling 146, relative to elongate tube 110, between an unexpanded or contracted position (FIG. 2) and an expanded or deployed position (FIG. 4). The unexpanded position corresponds to a first condition of gastric tube 100, as shown in FIG. 2, wherein distal portion 140b of sail member 140 extends within distal portion 136b of groove 136 of elongate tube 110 and is in substantially parallel relation to elongate tube 110. The expanded position corresponds to a second condition of gastric tube 100, as shown in FIG. 4, wherein distal portion 140b of sail member 140 is outside of distal portion 136b of groove 136 and is bowed outwardly from elongate tube 110. In the expanded position, sail member 140 defines a configuration that generally complements the curvature of a greater curvature portion "C2" of a stomach "ST" (FIG. 1).

Proximal portion 140b of sail member 140 may be grasped and manipulated relative to elongate tube 110 to transition sail member 140 between the unexpanded and expanded positions. As mentioned above, sail member 140 is dimensioned such that proximal portion 140a is accessible from outside the patient, thus readily enabling manipulation thereof. More specifically, translating sail member 140 distally relative to elongate tube 110 and through proximal portion 136a of groove 136 and coupling 146 urges sail member 140 distally through proximal portion 136a of groove 136 and coupling 146 such that distal portion 140b of sail member 140 is bowed outwardly relative to elongate tube 110 towards the expanded position. Translating sail member 140 proximally relative to elongate tube 110 pulls sail member 140 proximally through coupling 146 and proximal portion 136a of groove 136 such that distal portion 140b of sail member 140 is pulled inwardly relative to elongate tube 110 towards the unexpanded position and into distal portion 136b of groove 136.

Sail member 140 further includes a plurality of lights 148 disposed thereon and along an entirety of its length (FIG. 2). Lights 148 provide a visual reference of the position of sail member 140 and/or gastric tube 100 generally. Gastric tube 100 further includes a power source 150 in the form of a battery or some other power source to supply power to lights 148. Power source 150 is supported on proximal end portion 110a of elongate tube 110. It is contemplated that power source 150 can be a separate component of gastric tube 100. Alternatively, lights 148 may have an internal power source.

In operation, with sail member 140 in the unexpanded position, gastric tube 100 is inserted into a patient, such as, for example, an oral cavity "M" of a patient and is distally advanced toward a stomach "ST" of the patient along an enteral pathway "EP" that extends from the oral cavity "M," through an esophagus of the patient, and into the stomach "ST." Lights 148 are powered by power source 150 to illuminate sail member 140 and/or gastric tube 100 generally. With sail member 140 illuminated, gastric tube 100 is guided along the enteral pathway "EP" via observation of the illuminated sail member 140. Gastric tube 100 is selectively repositioned based on observed positions of the illuminated sail member 140 along the enteral pathway "EP." Gastric tube 100 is further guided through the esophagus and selectively positioned within the stomach "ST" of the patient. Gastric tube 100 is prevented from rotating out of the selected position due to the non-circular configuration of elongate tube 110.

Upon positioning gastric tube 100 within the stomach "ST," proximal portion 140a of sail member 140 is translated distally through proximal portion 136a of groove 136 relative to elongate tube 110. Distal movement of sail member 140, in conjunction with distal end 142 of sail member 140 being fixed with distal end 112 of elongated tube 110, causes distal portion 140b of sail member 140 to bow outwardly relative to elongate tube 110 towards the expanded position. As distal portion 140b of sail member 140 bows outwardly towards the expanded position, elongate tube 110 is urged towards and into complementary mating relation with the lesser curvature portion "C1" of the stomach "ST," while distal portion 140b of sail member 140 is urged towards and into complementary mating relation with the greater curvature portion "C2" of the stomach "ST." As such, the orientation of gastric tube 100 with elongate tube 110 extending along the lesser curvature portion "C1" of the stomach "ST" between the esophageal sphincter "E" and the pyloric sphincter "P can be readily achieved. As a result of this configuration of gastric tube 100 in the expanded position, the above-described orientation of gastric tube 100 within the stomach "ST" is maintained despite spasms, folding, spiraling, and/or shifting of the stomach "ST."

Once the proper orientation of elongate tube 110 has been achieved, suction is applied, by vacuum source "VS," within lumen 116 for suctioning any remaining contents within the stomach "ST" into lumen 116 of elongate tube 110 through apertures 128. Application of suction within lumen 116 also suctions the lesser curvature portion "C1" of the stomach "ST" to outer surface or periphery 118 of elongate tube 110, to ensure and maintain the complementary mating relation of elongate tube 110 with the lesser curvature portion "C1" of the stomach "ST."

With elongate tube 110 maintained in position relative to the lesser curvature portion "C1" of the stomach "ST" as a result of the applied suction, proximal portion 140a of sail member 140 is translated proximally relative to elongate tube 110 such that distal portion 140b of sail member 140 is pulled inwardly relative to elongate tube 110 and into distal portion 136b of groove 136. As suction is maintained at this point, elongate tube 110 is maintained in the position detailed above despite contraction of distal portion 140b of sail member 140.

Once distal portion 140b of sail member 140 has been returned to the unexpanded position (i.e., received in distal portion 136b of groove 136), transection of the stomach "ST" adjacent elongate tube 110 on an opposite side of elongate tube 110 relative to the lesser curvature portion "C1" of the stomach "ST" may be effected in any suitable fashion, e.g., using a stapling device or other suitable device. Transection in this manner reforms the stomach "ST" to a tubular-shaped configuration that generally approximates the outer dimension of elongate tube 110 and extends between the esophageal sphincter "E" and the pyloric sphincter "P." As can be appreciated, the diameter of elongate tube 110 may be selected in accordance with a desired diameter of the tubular-shape reformed stomach.

Figure 5:
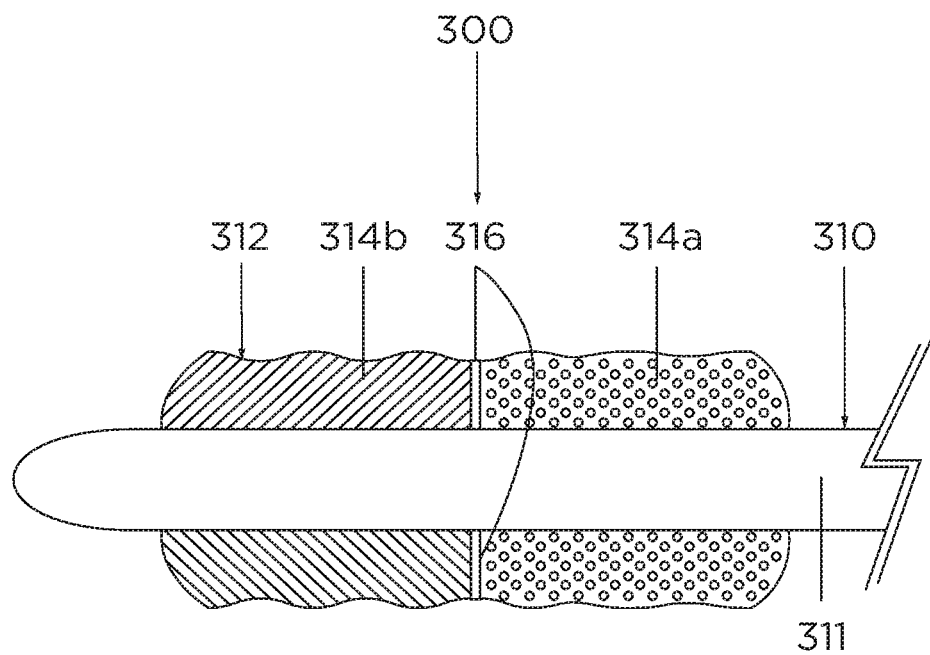
FIG. 5 is a cross sectional, side view of another embodiment of a gastric tube in accordance with the principles of the present disclosure.

In one embodiment, as shown in FIG. 5, a gastric tube 300, similar to gastric tube 100, is provided. Gastric tube 300 includes an elongate tube 310, similar to elongate tube 110, with the addition of a flexible tube or sheath 312 that encases at least a distal end portion 311 of elongate tube 300. The flexible sheath 312 includes two chambers 314a, 314b separated by a rupturable membrane 316. Each chamber 314a, 314b contains therein compositions or chemical compounds that chemiluminesce when combined.

In operation, elongate tube 310 is bent to rupture the membrane 316 separating the two chemical compounds such that the two chemical compounds combine or mix to chemiluminesce and illuminate elongate tube 310. Guidance of gastric tube 300 along the enteral pathway "EP" can be aided by constant visual verification of the location of the illuminated gastric tube 300.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described herein, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A gastric tube for use in a bariatric surgical procedure, comprising:
    an elongate tube defining a longitudinally-extending channel, the elongate tube having an outer surface defining a groove in the outer surface, the groove extending along a length of the elongate tube and separated from the longitudinally-extending channel by a wall of the elongate tube;
    a movable component supported in the groove of the elongate tube and movable between an unexpanded configuration in which the movable component is disposed within the groove and an expanded configuration in which at least a portion of the movable component extends outwardly from the outer surface of the elongate tube; and
    a sheath encasing a distal end portion of the elongate tube and including:
        a first chamber having a composition or chemical compound stored therein; and
        a second chamber having a composition or chemical compound stored therein, wherein the composition or chemical compound of the first chamber and the composition or chemical compound of the second chamber are chemiluminescent upon being combined.

2. The gastric tube according to claim 1, wherein the sheath includes a rupturable membrane that separates the first and second chambers from one another.

3. The gastric tube according to claim 1, wherein the groove includes:
    a proximal portion extending along a proximal end portion of the elongate tube; and
    a distal portion extending along distal end portion of the elongate tube.

4. The gastric tube according to claim 3, wherein the proximal portion of the groove has a first dimension, and the distal portion of the groove has a second dimension, different than the first dimension of the proximal portion.

5. The gastric tube according to claim 3, wherein the proximal portion of the groove has a smaller transverse cross-sectional area than the distal portion of the groove.

6. The gastric tube according to claim 1, wherein the movable component has a distal end portion that is fixedly coupled to distal end portion of the elongate tube.

7. The gastric tube as recited in claim 1, wherein the movable component has a distal portion releasably disposed within a distal portion of the groove such that the distal portion of the movable component is disposed outside of the distal portion of the groove when the movable component moves toward the expanded configuration.

8. The gastric tube as recited in claim 1, wherein the groove includes:
    a proximal portion configured to retain a proximal portion of the movable component as the movable component moves between the expanded and unexpanded configurations; and
    a distal portion configured to permit a distal portion of the movable component to move out of the distal portion of the groove when the movable component moves toward the expanded configuration.

9. The gastric tube as recited in claim 8, wherein the proximal portion of the movable component is slidably captured within the proximal portion of the groove such that the proximal portion of the movable component remains disposed within the proximal portion of the groove when the movable component moves toward the expanded configuration.

10. The gastric tube as recited in claim 1, wherein the outer surface of the elongate tube has an arcuate longitudinal side extending along the length of the elongate tube and a planar longitudinal side extending along the length of the elongate tube, the groove defined in the planar longitudinal side.

11. The gastric tube as recited in claim 1, wherein the longitudinally-extending channel of the elongate tube is a vacuum lumen.

12. The gastric tube as recited in claim 11, wherein the elongate tube has a proximal end portion defining an opening in communication with the vacuum lumen and configured to be coupled with a vacuum source.

13. The gastric tube as recited in claim 1, wherein the movable component has a plurality of lights disposed along a length thereof.

14. A method of performing bariatric surgery, comprising:
  activating a distal end portion of an elongate tube of a gastric tube to illuminate at least the distal end portion of the elongate tube, wherein activating the distal end portion of the elongate tube includes bending the distal end portion of the elongate tube to combine a composition or chemical compound stored within a first chamber of a sheath with a composition or chemical compound stored within a second chamber of the sheath;
  inserting the gastric tube into an oral cavity of a patient;
  guiding the gastric tube along an enteral pathway using the illuminated distal end portion of the elongate tube as a guide;
  repositioning the gastric tube to a selected position within a stomach of the patient; and
  moving a movable component of the gastric tube relative to the elongate tube from an unexpanded configuration toward an expanded configuration in which a distal portion of the movable component extends outwardly from an outer surface of the elongate tube into engagement with a portion of the stomach.

15. The method according to claim 14, wherein bending the distal end portion of the elongate tube includes rupturing a membrane of the sheath that separates the first and second chambers.

16. The method according to claim 14, wherein combining the composition or chemical compound stored within the first chamber of the sheath with the composition or chemical compound stored within the second chamber of the sheath results in chemiluminescence.

17. The method according to claim 14, wherein bending the distal end portion of the elongate tube includes bending the sheath which encases the distal end portion of the elongate tube.

18. The method according to claim 14, wherein moving the movable component includes sliding the movable component distally relative to the elongate tube and through a groove defined in an outer surface of the elongate tube, the groove extending along a length of the elongate tube.

* * * * *